(12) United States Patent
Duffner et al.

(10) Patent No.: US 7,029,842 B2
(45) Date of Patent: Apr. 18, 2006

(54) SIGNAL SEQUENCE TRAPPING

(75) Inventors: Fiona Duffner, København (DK); Reinhard Wilting, Farum (DK); Kirk Schnorr, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/823,825

(22) Filed: Mar. 30, 2001

(65) Prior Publication Data

US 2002/0076706 A1    Jun. 20, 2002

Related U.S. Application Data

(60) Provisional application No. 60/269,168, filed on Feb. 15, 2001, provisional application No. 60/249,237, filed on Nov. 16, 2000, provisional application No. 60/198,264, filed on Apr. 17, 2000.

(30) Foreign Application Priority Data

| Apr. 7, 2000 | (DK) | ................. 2000 00576 |
| Nov. 13, 2000 | (DK) | ................. 2000 01693 |
| Feb. 9, 2001 | (DK) | ................. 2001 00210 |

(51) Int. Cl.
*C12Q 1/00* (2006.01)
*C12P 19/34* (2006.01)
*C12N 15/00* (2006.01)
*C07H 21/02* (2006.01)

(52) U.S. Cl. ............... 435/6; 435/5; 435/91.1; 435/320.1; 435/DIG. 1; 435/DIG. 37; 536/23.1; 536/23.2

(58) Field of Classification Search .............. 435/6, 435/320.1, 69.1, 69.7, DIG. 1, DIG. 2, DIG. 3, 435/DIG. 4, DIG. 14, DIG. 15, 5, 7.4, 485, 435/463, DIG. 37, 29, 91.1, 91.41; 536/23.1, 536/23.4, 23.2

See application file for complete search history.

(56) References Cited

U.S. PATENT DOCUMENTS

| 5,948,622 A | * | 9/1999 | Reznikoff et al. | ............. 435/6 |
| 6,150,098 A | * | 11/2000 | Zhang et al. | ............. 435/6 |
| 6,468,739 B1 | * | 10/2002 | Haas et al. | ............. 435/6 |
| 6,562,624 B1 | * | 5/2003 | Adachi et al. | ............. 435/463 |

FOREIGN PATENT DOCUMENTS

| WO | WO 97/40146 | 10/1997 |
| WO | WO 98/13353 | 4/1998 |
| WO | WO 98/22491 | 5/1998 |

OTHER PUBLICATIONS

Smith et al., Journal of Bacteriology, Jul. 1987, p. 3321-3328.
Smith et al., Gene, 70 (1988) 351-361.
Hardouin et al., Genesis 26:245-252 (2000).
Manoil et al., Proc.Natl.Acad.Sci.USA, vol. 82, pp. 8129-8133, Dec. 1985.

* cited by examiner

*Primary Examiner*—Padmashri Ponnaluri
(74) *Attorney, Agent, or Firm*—Jason I. Garbell; Elias J. Lambiris

(57) ABSTRACT

The present invention allows the screening of previously established genebanks or libraries by proxy for genes encoding secreted, partially secreted, or cell surface-displayed polypeptides of industrial interest, such as enzymes, receptors, cytokines, peptide hormones etc. that would not likely have been isolated using conventional screening assays. A method for isolating genes encoding secreted, partially secreted, or cell surface displayed polypeptides from existing gene libraries is described in which the endogenous secretion signal sequences are detected using an in vitro polynucleotide insertion reaction where the inserted polynucleotide comprises a promoter-less and secretion signal-less secretion reporter.

10 Claims, 1 Drawing Sheet

SIGNAL SEQUENCE TRAPPING

CROSS-REFERENCE TO RELATED APPLICATIONS

Figure 1:
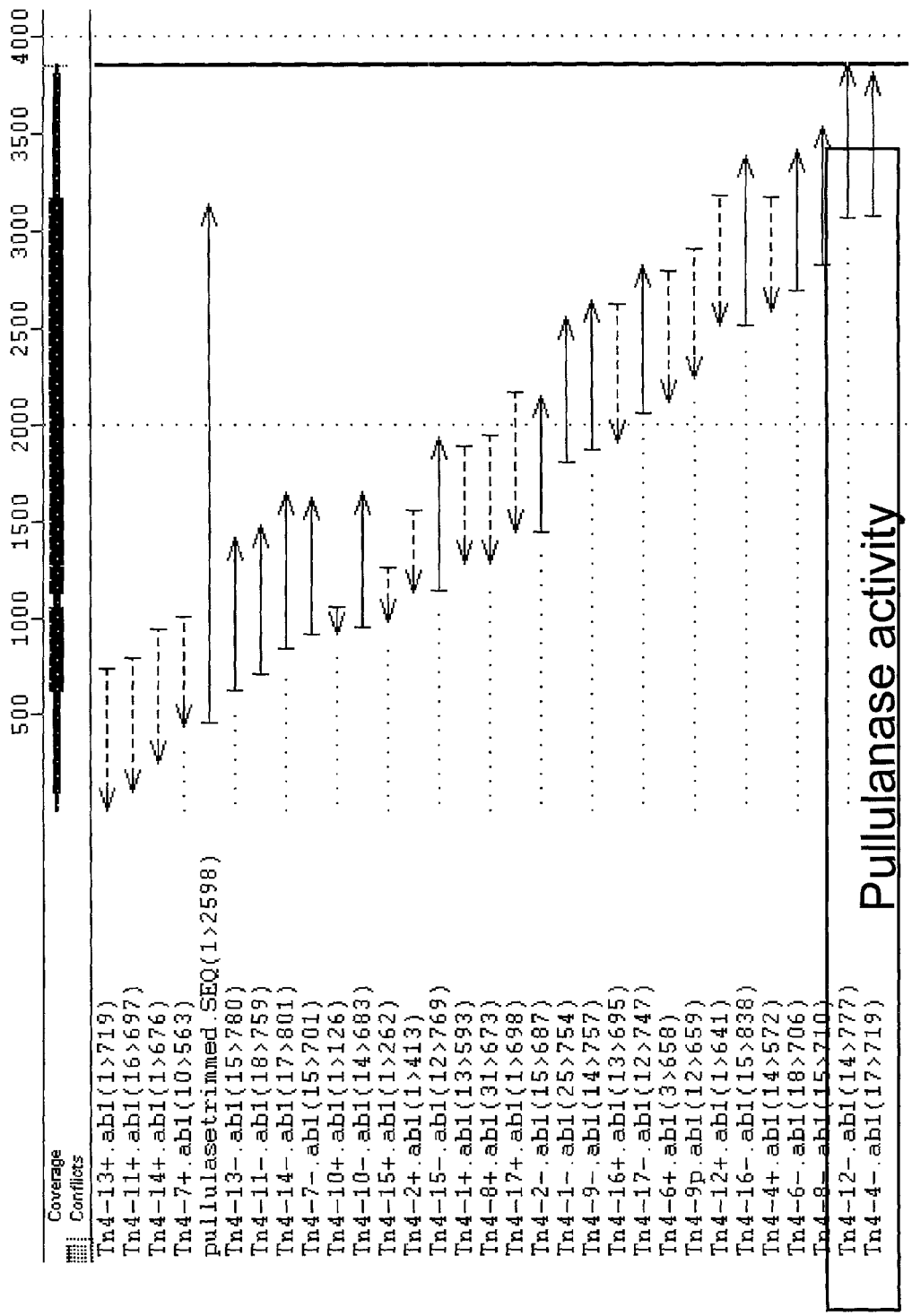

This application claims priority from Danish application nos. PA 2000 00576, PA 2000 01693 and PA 2001 00210 filed Apr. 7, 2000, Nov. 13, 2000 and Feb. 9, 2001, respectively, and U.S. applications Ser. Nos. 60/198,264, 60/249,237 and 60/269,168, filed Apr. 17, 2000, Nov. 16, 2000, and Feb. 15, 2001, respectively, the contents of which are fully incorporated herein by reference.

FIELD OF INVENTION

A method for isolating genes encoding secreted polypeptides from existing gene libraries is described in which the endogenous secretion signal sequences are detected using an in vitro transposition reaction where the transposon contains a secretion reporter.

BACKGROUND OF THE INVENTION

The search for new industrial enzymes and more specifically secreted enzymes is presently reliant on the availability of simple primary functional assays. Typically the substrate is used in the growth medium for the screening of microorganisms and degradation of the substrate may be recognized by a physical change in the substrate (colour change, halo formation around a colony, fluorescence etc.). Many proteins exist for which there is no simple functional assay and these may have potential application as industrial enzymes.

Enzymes which are secreted are highly interesting for use in industrial applications. A positive selection screening system which selects only clones encoding secreted enzymes is thus very desirable. Signal trapping is a method to identify genes containing a signal peptide using a translational fusion to an extracellular reporter gene lacking its own signal. This has been reported in the literature for the purpose of identifying new signal sequences (Manoil & Beckwith 1985, TnphoA: A transposon probe for protein export signals. Proc. Natl. Acad. Sci USA 82:8129–8133; Smith, H. et al., 1987, Construction and use of signal sequence selection vectors in *Escherichia coli* and *Bacillus subtilis*. J. Bact. 169:3321–3328), also the use of such for defining clearly the specific elements within signal peptides which are required for optimal function (Smith, H. et al, 1988. Characterisation of signal-sequence-coding regions selected from the *Bacillus subtilis* chromosome. Gene. 70:351–361).

A number of publications describe cloning vector reporter systems where genomic or cDNA libraries are constructed in a screening vector containing a signal-less reporter gene. When a cDNA or genomic fragment lacking a translational stop site is cloned upstream of the reporter gene in a translational fusion, a resulting protein-reporter gene fusion product is formed. If the cDNA or genomic fragment cloned contains a signal peptide, the fusion protein is secreted to the outside of the cell. Secretion can be detected by growth on selective media as in the use of invertase in *Saccharomyces cerevisiae* or in the use of e.g. β-lactamase in *Escherichia coli*. These publications are not concerned with methods for screening previously established gene libraries.

The number of clones to be investigated in the library is dramatically reduced by the screening to those containing a signal peptide, however a resulting clone may only contain an incomplete gene which may or may not include the minimum DNA information needed to encode the enzymatic activity originally associated with the secretion signal sequence isolated.

SUMMARY OF THE INVENTION

The problem to be solved by the present invention is to identify those clones in an existing gene library that encode efficiently secreted or surface-displayed polypeptides, even polypeptides with unknown activity, without having to redone a library in a screening-vector and without having to screen the library in traditional labour-and time consuming activity assays that would detect known activities only. Solving this problem allows rapid and efficient industrial exploitation of relevant secreted or surface-displayed polypeptides from new organisms from which gene libraries may already have been established previously.

We describe the combination of the use of a signal-less reporter gene and an in vitro polynucleotide insertion reaction for the identification of genes encoding secreted, partially secreted, or cell surface displayed polypeptides from genomic or cDNA libraries previously established, e.g. the use of a signal-less β-lactamase gene comprised in a transposon such as the MuA transposon. The present invention allows the screening of previously established genebanks or libraries by proxy for genes encoding secreted, partially secreted, or cell surface-displayed polypeptides such as enzymes, receptors, cytokines, peptide hormones etc. that would not likely have been isolated using conventional screening assays.

Accordingly in a first aspect the invention relates to a method for identifying and isolating a gene of interest from a gene library, wherein the gene encodes a polypeptide carrying a signal sequence for secretion or partial secretion, the method comprising the steps of:

(a) providing a genomic DNA library or a cDNA library;

(b) inserting into said library a DNA fragment comprising a promoterless and secretion signal-less polynucleotide encoding a secretion reporter;

(c) introducing the library comprising the inserted DNA fragment into a host cell;

(d) screening for and selecting a host cell that secretes or partially secretes the active secretion reporter;

(e) identifying the gene of interest into which the secretion reporter was inserted in the selected host cell, by sequencing the DNA flanking the inserted DNA fragment; and (f) isolating the complete gene of interest identified in step e).

In a second aspect the invention relates to a method for identifying and isolating a gene of interest from a gene library, wherein said gene encodes a polypeptide carrying a secretion signal sequence, the method comprising the steps of:

(a) providing a genomic DNA library or a cDNA library;

(b) inserting into said library a DNA fragment comprising a promoterless and secretion signal-less gene encoding a secretion reporter;

(c) introducing the library carrying random inserts of said DNA fragment into a population of host cells;

(d) screening for a host cell that expresses and secretes the secretion reporter;

(e) identifying the gene of interest into which the secretion reporter was inserted by sequencing the DNA flanking the DNA fragment of step b; and (f) isolating the complete gene of interest from the library of step a).

The terms "polypeptide""secreted"or "partial secretion" and "partially secreted" are used interchangeably herein and mean translocation of a part of a polypeptide or of a whole polypeptide across a membrane of a cell such as a prokaryotic, eukaryotic, or archaea cell. In a non-limiting example of polypeptide secretion, a membrane-bound or transmembrane protein such as a receptor may in the method of the invention be expressed in a host cell as a fusion polypeptide that is fused with the "secretion reporter" of the invention; thus "secretion" in this context means translocation of the fusion polypeptide across a membrane of the host cell to such an extent that at least the secretion reporter part of the fusion polypeptide is displayed on the extracellular side of the membrane and is functionally active in a secretion reporter assay. In other examples the fusion polypeptide may be completely secreted into the cultivation media without any residual linkage to the secreting cell.

In a non-limiting example herein, existing cDNA or genomic DNA libraries are tagged with a transposon containing a reporter gene. All in-frame fusions of the transposon reporter gene with a gene in the library containing a signal sequence are detected by assaying the expression of active reporter. The upstream and downstream flanking DNA sequences of the transposon insertion are then sequenced and the gene into which the transposon was inserted is identified by sequence analysis. In many cases, obtaining the full sequence of a tagged gene will be facilitated by the recovery of numerous clones of the same gene tagged in different nucleotide positions or sites. Positive clones are sequenced to identify clones that represent the same gene but have different transposon insertion sites. In this way all or most of the open reading frame (ORF) can be obtained by contig assembly. If a complete ORF cannot be obtained in this manner, perhaps due to an insufficient number or an uneven distribution of transposon inserts in the gene, then the full length gene may be obtained by classical primer walking DNA sequencing.

The sequence information thus obtained can then be used to isolate the complete gene of interest including the sequence encoding the secretion signal sequence and further to make an optimal expression construct for industrial production of the secreted proteins, all well within the skill of the art, whereafter the industrial production process of expressing and recovering the enzyme is a matter thoroughly described in the art as shown elsewhere herein.

Accordingly in a third aspect the invention relates to a gene of interest, wherein said gene is isolated by the method of the present invention, preferably the gene was isolated from a gene library. Another aspect of the invention relates to a gene of interest isolated from a gene library, wherein said gene is isolated by the method of the first or second aspect.

One aspect of the invention relates to an enzyme encoded by a gene of interest as defined in the previous aspects.

Further in another aspect the invention relates to an expression system comprising a gene of interest as defined in the previous aspects.

Yet other aspects of the invention relate to a host cell comprising an expression system as defined in the previous aspect, or to a host cell comprising at least two chromosomally integrated copies of a gene of interest as defined in the previous aspects.

In a final aspect the invention relates to a process for producing an enzyme comprising cultivating a host cell as defined in the previous aspects under conditions suitable for expressing a gene of interest as defined in the previous aspects, wherein said host cell secretes a protein encoded by said gene into the growth medium.

DRAWINGS

FIG. 1: Schematic alignment of the positions where a number of transposons were integrated into the gene encoding the pullulanase PULL1012. The known pullulanase coding sequence is indicated as "pullulanasetrimmed.SEQ (1>2598)" with an arrow pointing to the right to indicate direction of transcription. The positions of the transposons are indicated by arrows, one for each isolated clone, and clone designations are listed on the left. Clones where the β-lactamase secretion reporter was secreted are marked with a minus "–" in the designation and the indicative arrow points to the right showing co-directional transcription of the secretion reporter with the PULL1012 gene. Additional clones were isolated by ordinary selection that did not secrete the β-lactamase reporter; these are marked with a "+" or a "p", and the indicative arrow points to the left to show that an in-frame fusion, and thus a secreted fusion polypeptide, was impossible to achieve. The two clones "Tn4-12-.ab1" and "Tn4-4-.ab1" are boxed in the figure and the text indicates that the secreted fusion polypeptides retain the pullulanase activity encoded by the PULL1012 gene.

DEPOSITED MICROORGANISMS

A *Paenibacillus* NN018026 strain was deposited on 8 Feb. 2001 at DSMZ as DSM 14046.

Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: *A Laboratory Manual*, Second Edition (1989) Cold Spring Harbor Laboratory Press, Cold Spring Harbor, New York (herein "Sambrook et al., 1989") *DNA Cloning: A Practical Approach*, Volumes I and II/D. N. Glover ed. 1985); *Oligonucleotide Synthesis* (M. J. Gait ed. 1984); *Nucleic Acid Hybridization* (B. D. Hames & S. J. Higgins eds (1985)); Transcription And Translation (B. D. Hames & S. J. Higgins, eds. (1984)); *Animal Cell Culture* (R. 1. Freshney, ed. (1986)); *Immobilized Cells And Enzymes* (IRL Press, (1986)); B. Perbal, A Practical Guide To *Molecular Cloning* (1984).

When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the proteins in a highly purified form, i.e., greater than 95% pure, more preferably greater than 99% pure. When applied to a polynucleotide molecule, the term "isolated" indicates that the molecule is removed from its natural genetic milieu, and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, and may include naturally occurring 5' and 3' untranslated regions such as promoters and terminators. The identification of associated regions will be evident to one of ordinary skill in the art (see for example, Dynan and Tijan, Nature 316:774–78, 1985).

A "polynucleotide" is a single-or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Expression construct" is defined herein as a nucleic acid molecule, either single-or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, Streptomyces coelicolor agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta$\beta$-lactamase gene (Villa-Kamaroff et al., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in Scientific American, 1980, 242:74–94; and in Sambrook, J. et al., 1989, *Molecular Cloning, A Laboratory Manual*, 2d edition, Cold Spring Harbor, N.Y.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae enolase* (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for Saccharomyces cerevisiae enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15:5983–5990.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GALL system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

The introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, which are advantageously used in the method of the first aspects of the invention as well as in recombinant production of the polypeptides encoded by the gene of interest identified in the method of the invention. A vector comprising a nucleic acid sequence or gene of interest of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell for these purposes will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168:111–115), using competent cells (see, e.g., Young and Spizizin, 1961, *Journal of Bacteriology* 81:823–829, or Dubnau and Davidoff-Abelson, 1971, *Journal of Molecular Biology* 56:209–221), electroporation (see, e.g., Shigekawa and Dower, 1988, *Biotechniques* 6:742–751), or conjugation (see, e.g., Koehler and Thorne, 1987, *Journal of Bacteriology* 169:5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al, In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al, 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. BacterioL Symposium Series No. 9*, 1980).

In an even more preferred embodiment, the yeast host cell is a *Candida*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*.

In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81:1470–1474. Suitable methods for transforming *Fusarium* species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920.

Process of Production

The present invention also relates to processes for producing a polypeptide of the present invention comprising (a) cultivating a strain, which in its wild-type form is capable of producing the polypeptide, to produce a supernatant comprising the polypeptide; and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art.

For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. C. Janson and Lars Ryden, editors, VCH Publishers, New York, 1989).

DETAILED DESCRIPTION OF THE INVENTION

The present invention allows the screening of previously established genebanks or libraries by proxy, for genes encoding secreted polypeptides or enzymes even of unknown activity and thus without known screening assays. The method of the invention enables screening for polypeptides of potential industrial interest that would not likely have been isolated using conventional screening assays.

A method for identifying and isolating a gene of interest from a gene library, wherein the gene encodes a polypeptide carrying a signal sequence for secretion or partial secretion, the method comprising the steps of:

(a) providing a genomic DNA library or a cDNA library;

(b) inserting into said library a DNA fragment comprising a promoterless and secretion signal-less polynucleotide encoding a secretion reporter;

(c) introducing the library comprising the inserted DNA fragment into a host cell;

(d) screening for and selecting a host cell that secretes or partially secretes the active secretion reporter;

(e) identifying the gene of interest into which the secretion reporter was inserted in the selected host cell, by sequencing the DNA flanking the inserted DNA fragment; and (f) isolating the complete gene of interest identified in step e).

The present invention can be performed using any gene libraries known in the art, specifically it can also be used with gene libraries of viable but non-culturable organisms as typically seen in environmental samples. Processes of producing representative or normalized gene-libraries from environmental samples containing non-culturable organisms have been described in the art (U.S. Pat. No. 5,763,239).

Accordingly a preferred embodiment of the present invention relates to a method of the first aspect, wherein the complete gene of interest in step (f) is isolated from the library of step (a).

In the art several ways of inserting a DNA fragment into a genome are known, one example is insertion by transposition, however this usually requires time-and labour consuming mating experiments to be carried out. The present invention can be performed with ease using in vitro protocols commercially available as exemplified herein.

One preferred embodiment of the present invention relates to a method of the first aspect, wherein step b) is performed in vitro.

It may be an advantage in the method of the present invention to work with libraries wherein the representation of various DNAs are normalized, procedures for normalizing DNA libraries have been described in the art, see e.g. U.S. Pat. No. 5,763,239.

A preferred embodiment of the invention relates to the method of the first aspect, wherein the cDNA or the cDNA library is normalized.

Another preferred embodiment of the invention relates to the method of the first aspect, wherein the genomic DNA library or cDNA library is derived from a microorganism. In a preferred embodiment the microorganism is a fungus, a filamentous fungus or a yeast. In another preferred embodiment the microorganism is a bacterium, and in still another preferred embodiment the microorganism is an archaeon. Methods for establishing DNA or cDNA libraries from multicellular organisms are likewise well known in the art, such as from commercially available mammalian cell lines derived from insects such as the fruit fly or from plants or domestic animals, and even from humans. It may be of particular interest to use libraries derived from particular tissues or organs, such as the pancreatic gland of diabetic patients or cells from cancerous tumours.

In a preferred embodiment the invention relates to the method of any of the first aspect, wherein the genomic DNA library or cDNA library is derived from a multicellular organism, preferably from a mammalian cell, more preferably from a human cell.

As described elsewhere herein several methods exist in the art for random integration of DNA framents into larger DNA sequences, one preferred embodiment of the invention relates to the method of the first aspect, wherein the DNA fragment of the first aspect comprises a transposon, preferably a MuA transposon.

As described in an example herein it may be advantageous to use a DNA fragment of the invention which comprises an origin of replication that is functional in a host cell of the method of the invention.

Accordingly a preferred embodiment of the invention relates to the method of the first aspect, wherein the DNA fragment comprises an origin of replication which is functional in the host cell, preferably the origin of replication is functional in *Escherichia coli*, more preferably the origin of replication is a derivative of colE1, oriV, P15A, or colDF13, and most preferably the origin of replication is colE1.

A preferred embodiment of the invention relates to the method of the first aspect, wherein the secretion reporter is a protein which, when secreted from the host cells, allows said cells to grow in the presence of a substance which otherwise inhibits growth of said cells, preferably the secretion reporter is a β-lactamase or an invertase.

As mentioned elsewhere herein it may an advantage in the method of the invention if the polynucleotide of the DNA-fragment of steb (b) in the method encodes a secretion reporter carrying an N-terminal peptide linker which comprises a specific target site for proteolytic cleavage. Thus when the DNA-fragment is inserted in frame into a gene of interest encoding a secreted or partially secreted polypeptide the resulting fusion polypeptide will comprise the following components: secreted polypeptide—peptidelinker—secretion reporter. Accordingly when a particularly interesting gene of interest is identified, it is straightforward to cleave the fusion polypeptide and isolate the encoded polypeptide without the secretion reporter, similar fusion polypeptide approaches are well described in the art (see e.g.: WO 00/75344). In the present context, when at least two genes and maybe other DNA elements are linked together to form one single open reading frame, and these elements are expressed into one polypeptide in the same order as they are listed, the elements are said to be "sequentially fused" or "fused sequentially" and the polypeptide is referred to as a "fusion polypeptide" or "fusion protein"

By the term "linker" or "spacer" is meant a polypeptide comprising at least two amino acids which may be present between the domains of a multidomain protein, for example an enzyme comprising a core enzyme and a binding domain such as a cellulose binding domain (CBD) or any other enzyme hybrid, or between two proteins or polypeptides expressed as a fusion polypeptide, for example a fusion protein comprising two core enzymes or a fusion protein as the one present in the cell of this invention. For example, the fusion protein of two core enzymes is provided by fusing a DNA sequence encoding the first core enzyme, a DNA sequence encoding the linker and a DNA sequence encoding the second core enzyme sequentially into one open reading frame and expressing this construct. A linker may also comprise a target site for proteolytic cleavage.

The target site of proteolytic cleavage is, in a preferred embodiment of the invention, an amino acid sequence, which is recognized and cleaved by a protease. Several amino acid sequences have been described in literature that strategically located will promote efficient cleavage of a fusion product. Most of these strategies involve site-specific proteolytic cleavage in a linker region between the mother enzyme and the wanted peptide (Polyak et al. (1997) Protein Engineering, Vol. 10 (6) pp. 615–619; Kjeldsen et al. (1996) Gene, Vol. 170 (1) pp. 107–112; Sun et al. (1995) Protein Expression and Purification, Vol. 6 (5) pp. 685–692; Martinez et al. (1995) Biochemical Journal, Vol. 306 (Pt 2) pp. 589–597).

In order to ensure efficient cleavage one could insert an amino acid sequence between the mother enzyme and the exogenous polypeptide (in this case the secretion reporter encoded by the DNA fragment of the method of the invention), which codes for a recognition site for a site-specific protease. Several combinations of recognition site and proteases have been described in literature. The Kex2 proteinase hydrolyzes peptides and proteins with basic amino acid pairs which are cleaved at the C-ends of their peptide bonds (Bessmertnaya et al. (1997) Biochemistry, Vol. 62 (8) pp. 850–857. The Kex2 cleavage site used in one preferred embodiment according to the first and second aspects is the Lys-Arg (K-/-R) sequence, but other combinations of basic amino acids could be inserted to optimize the cleavage by Kex2 (Ledgerwood. et al. (1995) J.Biochem., Vol. 308 (1) pp. 321–325; or Ghosh, S. et al. (1996) Gene (Amsterdam), Vol. 176 (1–2) pp. 249–255).

Other useful combinations of proteases and cleavage sitesare: Enterokinase (La Vallie et al. (1993) J.Biol.Chem., Vol 268 pp.2311–2317) with a preference for cleaving the amino acid sequence X-D-D-D-K-/-X, Trypsin (Jonasson et al. (1996) Eur.J.Biochem., Vol 236 (2) pp. 656–661) with a preference for cleaving the amino acid sequence X-K-R-/-X, Factor Xa (Nagai et al. (1985) PNAS, Vol 82 pp. 7252–7255) with a preference for cleaving the amino acid sequence X-I-E-G-R-/-X, Collagenase (Chinery et al. (1993) Eur.J.Biochem., Vol 212 (2) pp. 557–553) with a preference for cleaving the amino acid sequence P-X-I-G-P-X-X, Thrombin (Rahman et al. (1992) Cell.Mol.Biol., Vol 38 (5) pp. 529–542) with a preference for cleaving the amino acid sequence X-G-V-R-G-P-R-/-X, ALP (Achromobacter lyticus Lys-specific protease) (Kjeldsen et al., (1996) Gene, Vol 170 (1) pp. 107–112) with a preference for cleaving at Lysine, and the C-component protease from *Bacillus licheniformis* cleaving at Glu (Kakudo et al. (1992) J.Biol.Chem., Vol 267 (33) pp. 23782–23788).

Another preferred method of cleaving a peptide at a specific target site is by using chemical compounds such as cyanogen-bromide which cleaves X-M4-X or hydroxylamine which cleaves S-N-/-G-X (Current protocols in Molecular Biology. John Wiley and Sons, 1995; Harwood, C. R., and Cutting, S. M.(eds.)).

A preferred embodiment of the invention relates to the method of the first aspect, wherein the polynucleotide of the DNA-fragment of step (b) encodes a secretion reporter carrying an N-terminal peptide linker which comprises a specific target site for proteolytic cleavage.

For the present invention several host cells can be imagined to work well, the only criterion being that the host cell recognizes the secretion signal sequence of the gene of interest, and that the host cell is capable of synthesizing a functional secretion reporter.

A preferred embodiment of the present invention relates to the method of the first aspect, wherein the host cell is bacterial, preferably the bacterial cell is an *Escherichia, Lactococcus, Streptomyces, Enterococcus* or *Bacillus* cell, preferably of the species *Escherichia coli, Lactococcus lactis, Streptomyces griseus, Streptomyces coelicor, Enterococcus faecalis, Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* or *Bacillus thuringiensis.*

A preferred embodiment of the present invention relates to the method of the first aspect, wherein the host cell is fungal, preferably the fungal cell is of the genus *Candida, Kluyveromyces, Pichia, Saccharomyces, Schizosaccharomyces, Yarrowia, Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma,* more preferably the fungal host cell is of the species *Saccharomyces cerevisiae, Aspergillus aculeatus, Aspergillus awamori, Aspergillus nidulans, Aspergillus niger,* or *Aspergillus oryzae.*

The fungal host cell of the invention may be *Saccharomyces carisbergensis, Saccharomyces cerevisiae, Saccharomyces diastaticus, Saccharomyces douglasii, Saccharomyces kluyveri, Saccharomyces norbensis, Saccharomyces oviformis, Aspergillus aculeatus, Aspergillus awamori,*

*Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride.*

In yet another preferred embodiment, the host cell is mammalian, preferably human, more preferably a HeLa-cell. Non-limiting well known examples of mammalian cells include CHO (Chinese hamster ovary), NIH3T3, WRL-68, CoLo587, PANC-1, HeLa S3, K562, Raji, SW480, Soares B cells (Human), Sp2/O-AG14 (*Murine myeloma*), BHK-21 cells (Baby hamster kidney), Sf9 *Spodoptera frugiperda* (insect), D-MEL-2 *Drosophila melanogaster* (fruit fly, insect); all commercially available from ATCC.

The method of the present invention relies on DNA sequence information to isolate the gene of interest as exemplified elsewhere herein.

Accordingly a preferred embodiment of the invention relates to the method of the first aspect, wherein the sequencing step is done using at least one primer directed to the DNA fragment of the first aspect, or using at least one primer directed to a vector in which the DNA library or cDNA library of the first aspect is cloned.

Further a preferred embodiment of the invention relates to the method of the first aspect, where isolating the complete gene of interest is done utilizing the DNA sequence information obtained in the sequencing step of the first aspect.

The gene of interest to be isolated by the method of the present invention may encode any polypeptide such as a polypeptide with pharmaceutical properties, a peptide hormone, an antibody or an antibody fragment, a receptor, or an enzyme.

Consequently a preferred embodiment of the invention relates to the method of the first aspect, wherein the complete gene of interest encodes an enzyme that is secreted from the host cell.

Cytokines are secreted regulatory peptides that mediate a wide range of biological activities by binding to specific cell surface receptors on target cells. Cytokine actions include control of cell proliferation and differentiation, regulation of hemopoiesis and immune and inflammatory responses. Cytokines are also major orchestrators of host defence processes and as such are involved in responses to exogenous as well as endogenous insults and in repair or restoration of tissue integrity (Shi et al., 2000. J. Biol. Chem. 275:19167–19176).

Identification of novel members of the cytokine family and their receptors is of great importance because they play key roles in regulating a broad-range biological response. Cytokines have a highly conserved 4-helix bundle tertiary structure but have a low homology in the primary amino acid sequence. Therefore, identification of novel cytokines using homology-based cloning methods has been rather difficult. The molecular cloning of a novel cytokine receptor may help to understand the pathogenesis of some disease and to tailor treatments accordingly.

Most members of the type 1 cytokine receptor family have been cloned using ligand binding as an assay. Alternatively, oligonucleotides for the WSXWS motif were used as hybridization probes, and degenerate polymerase chain reaction (PCR) with primers for the highly conserved region of type 1 cytokine receptors was also used. Nowadays, some cytokine receptors can be identified in a search of expressed sequence tag (EST) database as a result of homology with known cytokine receptors (Sprecher CA, et al., Cloning and characterization of a novel class I cytokine receptor. Biochem Biophys Res Commun. 1998; 246:82), (Elson GC, et al., Cytokine-like factor-1, a novel soluble protein, shares homology with members of the cytokine type 1 receptor family. J. Immunol. 1998; 161:1371) or using signal sequence prediction of cDNA expressed sequence tags (ESTs) (Shi, Y. et al., 2000, A novel cytokine receptor ligand pair, J. Biol. Chem. 275:19167–19176).

A method termed SST-REX (signal sequence trap by retrovirus-mediated expression screening) using signal trapping was described, where the cDNA library was constructed in a retrovirus vector, transfected into host cells and screened for their ability to redirect a constitutively active mutant of a cytokine receptor to the cell surface, thereby allowing interleukin-3 (IL-3)-independent growth of otherwise IL-3-dependent Ba/F3 cells. (Kojima, T. and Kitamura, T., 1999, A signal sequence trap based on a constitutively active cytokine receptor, Nature Biotech 17:487–490). The present invention increases the chance of finding full length genes encoding cytokines and sequencing of the genes is easily facilitated thus allowing a more rapid discovery of new cytokines.

Another preferred embodiment of the invention relates to the method of the first aspect, wherein the complete gene of interest encodes a membrane-bound receptor, preferably a two-component signal (TCS) transduction receptor, and more preferably a cytokine receptor.

Still another preferred embodiment of the invention relates to the method of the first aspect, wherein the complete gene of interest encodes a secreted polypeptide cytokine.

Surface structures and secreted factors from pathogens have a potential value as vaccines. Those surface structures and secreted factors that are proteins are synthesised inside the pathogenic cells and are secreted to the surface or into the extracellular space of the cells. The present invention may be used to identify such proteins, which can later be tested for antigenicity. Non-limiting examples of secreted proteins from pathogenic cells that may be used to generate vaccines are: lipoproteins, periplasmatic proteins, inner membrane proteins and outer membrane proteins.

Several such proteins from *Neisseria gonorrhoeae* were selected as potential vaccine targets and were tested for their suitability in vaccine generation (Pizza et al. (2000) Nature 287:1816–1820). The pathogenic *Neisseria* species causes significant morbidity and mortality in children and adults worldwide. *Neisseria meningitidis* has become the leading cause of bacterial meningitis in children and young adults in the US. In Europe and North America, between one fourth and two thirds of meningococcal disease isolates are serogroup B. Unlike serogroups A and C for which a polysaccharide vaccine is currently available, the serogroup B polysaccharide is poorly immunogenic in all age groups (Bash MC, et al., 2000, Genetic and immunologic characterization of a novel serotype 4, 15 strain of *Neisseria*, FEMS Immunol Med Microbiol, 29(3): 169–176).

Outer membrane protein (OMP) vaccines are being investigated to address the need for protection against group B meningococcal disease (Zollinger, W.D., 1997, New and improved vaccines against meningococcal disease. In: New Generation Vaccines (Levine, M. M. et al., Eds.), 2nd ed., pp. 469–488. Marcel Dekker, New York).

Non-limiting preferred examples of proteins that may used to generate vaccines are: the outer membrane protein MtrE (multiple drug resistence) of *Neisseria ghonorrhoeae*; the secreted protein Ag85 from *Mycobacterium tuberculosis*, which is a secreted antigen identified in the BCG (bacilli Calmette Guerin) (Tyagi AK (2000) FEMS Microbiol Lett. 190:309–316); the outer membrane protein OprM (multiple drug resistance) from *Pseudomonas aeruginosa*; and the following secreted proteins (Molekulare Infektionsbiologie ed.: Hacker, J. Heesemann, J, Heidelberg; Berlin; Spektrum, Akad. Verlag 2000):

*Yersinia* ssp.: outer proteins (YOPs) type III such as YopE, H, M, O.

*Pseudomonas syringae*: ArvB protein.

*Pseudomonas aeruginosa* ExoS cytotoxin.

*Neisseria* ssp. IgA protease, Typ IV fimbriae.

*Escherichia coli* a-Haemolysin HylA, EPEC Intimin (EaeA) invasin, P-fimbrien (Pap), S-Fimbrin.

Entobacteria Typ I fimbriae.

Surface structures and secreted factors of pathogens can be used for diagnostics. They can be used to obtain antibodies directed against the pathogens structures or secreted factors. Those surface structures and secreted factors that are proteins are synthesised inside the pathogens cells and are secreted to the surface or into the extracellular space of the cells. The present invention may be used to identify such proteins. Non-limiting examples of secreted proteins that may be used to generate diagnostic antibodies are listed above, since proteins that are suitable for generating vaccines are equally suitable in diagnostic assays.

An application for the present invention may be cloning of secreted allergens for immune therapy. Typically human allergens comprise proteins. Such proteins, when isolated, may be used for inducing tolerance of the allergen e.g. via subcutaneous administration of the allergen (See: WO 93/19178; WO 99/34826; U.S. Pat. No. 6,048,962; U.S. Pat. No. 5,558,869; WO 98/04274; U.S. Pat. No. 6,147,201; U.S. Pat. No. 5,693,495; or U.S. Pat. No. 5,958,891).

Listed below are non-limiting examples of major human proteinaceous allergens that are secreted from cells: Human T cell reactive feline protein; Der f II Major house dust mite allergen; AMBTv Ragweed pollen major allergen; 5C Lolium perenne pollen allergen; cry j 2 Japanese ceder allergen; Alt a 1 Alternaria alternata major allergen; and Ara h 1 Peanut allergen.

Via the transposon assisted signal sequence trapping method of the present invention we may be able to identify genes encoding membrane bound proteins, and as mentioned above, membrane-bound proteins may have a huge potential in the development of vaccines. Membrane-bound proteins include lipoproteins, receptors for solute uptake, quorum sensing receptors and parts of bacterial two-component regulatory systems (TCS) that play a pivotal role in the process of infection. Signal transduction systems like TCS enable bacterial pathogens to mount an adaptive response and cope with diverse environmental stresses, including nutrient deprivation, antibiotic onslaught and phagocytosis.

Interest in TCS as novel bacterial targets has been rekindled by the recent discovery of several essential systems in important Gram-positive and Gram-negative pathogens (Inhibitors of bacterial two-component signalling systems, Macielag MJ; Goldschmidt R Expert Opinion on Investigational Drugs, Vol. 9 (10) pp. 2351–2369 (2000)).

The present invention allows the cloning of cell wall attached proteins that are of huge commercial interest. Because of the unique chemistry and the necessity of selectively cleaving old stress-bearing wall for growth, the wall of the bacterial cell has been a key target for chemotherapeutic treatment of bacterial diseases (*Koch AL* Critical Reviews in Microbiology, Vol. 26 (1) pp. 1–35 (2000)). Currently, many infectious organisms are becoming resistant to overused antibiotics. Still the wall is a good target, and there could possibly be several entirely new classes of antibiotics targeted toward other parts of wall metabolism and function. The essential autolysins may be a particularly relevant target.

Other proteins which can be found identified using the present invention include the adhaesins, such as the following: P-fimbriae (Pap) of uropathogenic *E. coli*, S-Fimbriae, Type IV fimbriae of *Neisseria* and Type I fimbriae of entobacteria and Invasins for example EPEC: Intimin (EaeA) invasin. (Molekulare Infektionsbiologie ed.: Hacker, J. Heesemann, J, Heidelberg; Berlin; Spektrum, Akad. Verlag 2000).

Accordingly a preferred embodiment of the invention relates to the method of the first aspect, wherein the complete gene of interest encodes a polypeptide which elicits an immunogenic response in humans.

Bacteriocins are small peptides that have antimicrobial activity against different bacteria. They are synthesised by some bacterial and eukaryotic species. Examples are: Leucocin A, Pediocin PA-1, Enterocin A and P, Sakacin A and P and Nisin. Bacteriocins can be used to protect food against bacterial contamination and are of potential commercial value in the food industry. Since bacteriocins are mostly secreted peptides that are transported to the extracellular space the encoding genes may be isolated via the signal trapping method of the present invention by using a suitable host organism and a suitable secretion reporter gene. To isolate bacteriocins that are secreted in a sec-dependent manner a sec-dependent reporter may be used e.g. betaβ-lactamase.

A large number of bacteriocins have been characterized in recent years, most of the new bacteriocins belong to the class 11 bacteriocins, which are small (30–100 amino acids) heat-stable proteins that are usually not post-translationally modified. Based on common features, some of the class 11 bacteriocins can be subdivided into groups such as the pediocin-like and the strong anti-listeria bacteriocins, the two-peptide bacteriocins, and bacteriocins with a sec-dependent signal sequence. With the exception of the very few bacteriocins containing a sec-dependent signal sequence, class 11 bacteriocins are synthesised in a preform containing an N-terminal double-glycine leader sequence. The double-glycine leader-containing bacteriocins are processed concomitantly with cellular externalization by a dedicated ABC-transporter system which has been shown to possess an N-terminal proteolytic domain (Nes, I.F., et al., 1996, Int J Gen Mol Microbiol 70:113–128).

A preferred embodiment of the invention relates to the method of the first aspect, wherein the complete gene of interest encodes a bacteriocin.

Many pathogenicity factors of plant pathogenic bacteria, fungi and other microorganisms are secreted proteins e.g. the vir genes of *Agrobacterium tumefaciens* encode secreted proteins that mediate the tDNA transfer from the bacterium into the plant cell. This transfer is essential for the pathogenicity of the *A. tumefaciens*. Also fungal species like e.g. *Ustilago maydis*, the cause of corn smut disease, secrete proteins that are involved in the pathogenicity of the fungus. Other bacterial plant pathogens are *Pseudomonas* ssp., *Xanthomonas* ssp., and *Stenotrophomonas* ssp. The method of the present invention may be used to isolate genes encoding the secreted proteins involved in plant pathogenicity and these proteins may in turn be used to design inhibitors for the secreted proteins.

Accordingly a preferred embodiment of the invention relates to the method of the first aspect, wherein the complete gene of interest encodes a plant pathogenic polypeptide.

As mentioned previously the method of the invention can be used to isolate a gene of interest to be expressed in an industrial scale later, however this would likely require the construction of an expression system such as described in the art and referenced elsewhere herein.

A preferred embodiment of the invention relates to the method of the first aspect, wherein an additional step of constructing an expression system is performed, said expression system comprising the complete gene of interest isolated in the first aspect.

A gene of interest, wherein said gene is isolated by the method of the present invention, preferably the gene was isolated from a gene library.

An enzyme encoded by a gene of interest as defined in the previous aspect.

An expression system comprising a gene of interest as defined in the previous aspects.

A host cell comprising an expression system as defined in the previous aspects.

A host cell comprising at least two chromosomally integrated copies of a gene of interest as defined in the previous aspects.

A process for producing a polypeptide comprising cultivating a host cell as defined in the previous aspects under conditions suitable for expressing a gene of interest as defined above, wherein said host cell secretes a polypeptide encoded by said gene into the growth medium.

A preferred embodiment of the invention relates to the process of the final aspect, wherein the polypeptide is an enzyme.

Finally a preferred embodiment of the invention relates to the process of the final aspect, where an additional step of purifying the polypeptide is performed.

EXAMPLES

Example 1

Construction of a SigA transposon containing the β-lactamase reporter gene. This example utilizes a β-lactamase from which the secretion signal has been removed. The β-lactamase conveys ampicillin resistance on *E. coli* only when the protein is secreted to the periplasm, cytoplasmic expression of β-lactamase does not confer ampicillin resistance. Without a signal sequence the β-lactamase enzyme will not be transported to the periplasm and therefore that clone will not grow on media containing ampicillin. A β-lactamase gene is transferred to the target clone using in vitro transposition of the transposon described below.

The construction of a transposon containing a signal-less β-lactamase gene was carried out using standard molecular biology techniques. The signal-less β-lactamase gene was initially PCR amplified from commercially available sources (such as from the vector pUC19) using a proofreading polymerase (Pfu Turbo for example). The resulting PCR fragment contained the restriction sites NotI and EcoRi in order to aid cloning.

The mini-transposon MuA encoding chloramphenicol resistance was PCR amplified from a commercially available kit (Finnzymes) using a proof reading polymerase (Pfu Turbo) and the primer MuA-F (SEQ ID NO:1): 5'-GM-GATCTGAAGCGGCGCACGA. The resulting transposon containing PCR fragment was purified and ligated into the vector pKl 84 containing a kanamycin resistance gene.

The ligation mixture was electroporated into *E. coli* DH10B and clones containing pK184 with the transposon fragment inserted were selected on LB medium containing chloramphenicol and kanamycin. Many colonies were recovered and plasmid DNA was isolated from 10 of them. Sequencing revealed the correct insertion of the signal-less β-lactamase gene into the transposon MuA contained on the plasmid pK184 (Jobling M. G., Holmes R. K. 1990. Construction of vectors with the p15a replicon, kanamycin resistance, inducible lacZalpha and pUC18 or pUC19 multiple cloning sites. Nucleic Acids Res. 18:5315–5316).

The signal-less β-lactamase gene is contained within the transposon in such a way that there is a continuous open reading frame between the transposon border region (approximately 50 bp in the case of MuA) and the β-lactamase coding region. In this way the modified transposon, when it transposes into a gene encoding a protein that is secreted, can cause an in-frame fusion with the target gene. This results in a fusion gene product that is secreted to the periplasm of *E. coli* and conveys resistance to the ampicillin. Not all transposition events into secreted genes will result in a successful in-frame fusion but when using a positive selection we can screen high numbers and thereby select for even very infrequent events.

Example 2

Construction of a SigA2 transposon containing the β-lactamase reporter gene. The construction of a transposon containing a signal-less β-lactamase gene was carried out using standard molecular biology techniques. The signal-less β-lactamase gene was initially PCR amplified from the vector pUC19) using a proofreading polymerase (Pfu Turbo, Stratagene, USA). The resulting PCR fragment contained the restriction sites NotI and EcoRl in order to aid cloning. The plasmid pEntranceposon(Cam) containing the Entranceposon and the antibiotic resistance markers CAT (encoding chloramphencol resistance in the transposon) was obtained from Finnzymes, OY (Espoo Finland). The plasmid was digested with the restriction enzymes NotI and EcoRI, gel purified and ligated with the signal-less β-lactamase containing fragment. The ligation was transformed into electrocompetent DH10B cells and the *E. coli* clone containing the recombinant plasmid with the signal-less β-lactamase was identified by restriction analysis and named *E. coli* SigA2. Plasmid DNA from *E. coli* SigA2. was isolated using the QiaSpin protocol and digested with Bglll. The DNA fragment containing the transposon was gel purified using the GFX protocol. This DNA fragment is the transposon containing the signal-less β-lactamase and is called SigA2.

Example 3

Use of the SigA transposon containing a signal-less β-lactamase as a reporter gene in the signal trapping of the extracellular xyloglucanase XYG1006.

First the sigA minitransposon is transposed into a cloned subgenomic fragment that contains a known gene encoding an assayable secreted gene-product. In this example we use a xyloglucanase from *Paenibacillus polymyxa*. The xyloglucanase is a large open reading frame (3036 bp) on a subgenomic clone fragment of 4.6 kb in size obtainable from the plasmid in *Escherichia coli* DSM 13321.

Step 1: Linear mini transposons were prepared by PCR of psigA with Pfu turbo polymerase (Stratagene Inc., USA) using the primer muA-f (SEQ ID NO: 1) amplifying the entire mini transposon. The mini transposons were purified using a GFX column (Pharmacia), diluted to 23ng/ul and used in the standard Finnzyme GPS transposition protocol.

Step 2: The signal trapping mini transposon sigA, the plasmid pXYG1006, 5X buffer and the transposome were mixed in an Eppendorf® tube in the appropriate concentrations and the in vitro transposition reaction was performed according to the original Finnzymes protocol. A control experiment using the same plasmid with the original CAM minitransposon was performed in parallel. The transposition reactions were transformed into *E. coli* XL1-blue electrocompetent cells (Stratagene, USA) by electroporation in a Biorad Gene Pulse device (50 uF, 25 mAmp, 1.8 kV). The cells were diluted in 1 ml SOC media and preincubated in a 37° C. shaker for one hour. Appropriate dilutions were plated on the LB solid medias listed below to determine the transformation, transposition and signal trapping efficiency as shown in table 1.

Solid LB media
LB-kan (50 mg/ml kanamycin).
LB-CAM (10 mg/ml chloramphenicol).
LB-CAM-AMP (10 mg/ml chloramphenicol, 100mg/ml ampicillin).
LB-CAM, amp, AZCL-xyloglucan (10 mg/ml chloramphenicol, 50 mg/ml ampicillin, 0.07% w/v AZCL-xyloglucan).

Colonies growing on LB-CAM-AMP were replica plated on LB-CAM-AMP AZCL-xyloglucan to obtain the frequency of disruption of the xyloglucanase domain which is in the first 900 bp of the ORF.

TABLE 1

Typical results of transposition into pXYG1006

| Selection media | Transformants per μg plasmid DNA | |
| --- | --- | --- |
| | PSigA | CAM transposome |
| LB-kanamycin | $3.3 \times 10^8$ | $10^9$ |
| LB-CAM | $7.5 \times 10^6$ | $10^6$ |
| LB-CAM-AMP | $10^4$ | 0 |
| LB-CAM-AMP AZCL xyloglucan | $10^3$ | 0 |

The *E. coli* clones selected on ampicillin and chloramphenicol were those where the β-lactamase reporter gene made a translational fusion with the XYG1006 xyloglucanase gene so hat the XYG1006 signal peptide caused the transport of β-lactamase to the periplasm of *E. coli*. Sequencing confirmed that all positive clones contained the transposon downstream of the signal sequence. Plasmid DNA from ten random ampicillin resistant colonies was prepared using the Qiaspin procedure (Qiagen) and DNA sequences were determined from the plasmids using two primers specific for the transposon:

```
SigA-r (SEQ ID NO:2):   GCACCCAACTGATCTTCAGCA, and

SeqB (SEQ ID NO:3):     TTATTCGGTCGAAAAGGATCC; or

SigA2up (SEQ ID NO:4):  AGCGTTTGCGGCCGCGATCC, and

SeqB (SEQ ID NO:3).
```

Analysis indicates that the SigA transposon landed in the XYG1006 coding region in frame with the xyloglucanase open reading frame. A typical example of an in frame fusion of the β-lactamase gene with the native signal peptide of XYG1006 is as follows:

Clone
pSigA2-11 was isolated as a signal colony that was capable of growing on plates under double selection (LB-CAM-AMP). Plasmid DNA was prepared from this isolate using the Qiaspin™ plasmid prep kit (Qiagen GMBH). The plasmid DNA was sequenced using the primers SeqA and SeqB (Finnzyme Inc.) in a ABI Prizm 377 sequencer using the ABI sequencing kit to perform the reactions. DNA Sequence analysis of clone pSigA2-11 indicated that the SigA2 transposon was inserted 58 bp from the ATG start codon of the xyloglucanase encoding gene, XYG1006, in such a manner as to make an in frame fusion between the gene and the secretion reporter β-lactamase gene. This resulted in the 19 amino acid secretion signal peptide being fused to the β-lactamase peptide, which effectively targeted the β-lactamase enzyme to the periplasm of *E. coli*.

Example 4

Use
of the transposon SigA2 containing a signal-less β-lactamase as a reporter gene in he signal trapping of the extracellular pullulanase PULL1012.

First
the SigA2 minitransposon was transposed into a cloned subgenomic fragment that contained a known gene encoding an assayable secreted gene-product. In this example we used the PULL 1012 pullulanase encoding gene from *Anaerobranca horikoshii* DSM 9786. The pullulanase is encoded by a large open reading frame (2597 bp) on a subgenomic clone ragment of 3054 bp in size. The SigA2 mini transposons were purified using a GFX column (Pharmacia), the pure DNA was diluted to 20ng/ul and used in the standard Finnzyme GPS transposition protocol.

The
signal trapping mini transposon SigA2, the plasmid pPULL1012, 5X buffer and the MuA transposase were mixed in an Eppendorf® tube in the appropriate concentrations and the in vitro transposition reaction was performed according to the original Finnzymes protocol. The transposition reactions were transformed into *E. coli* DH10B electrocompetent cells (Stratagene, USA) by electroporation in a Biorad Gene Pulse device (settings: 50 uF, 25 mAmp, 1.8 kV). Following electroporation the cells were diluted in 1 ml SOC media, pre-incubated in a 37° C. shaker for one hour and plated on LB agar containing kanamycin, ampicillin and chloramphenicol.

The
*E. coli* clones selected on kanamycin, ampicillin and chloramphenicol were those where the β-lactamase reporter gene made a translational fusion with the PULL1012 pullulanase gene so that the PULL1012 signal peptide caused the transport of β-lactamase to the periplasm of *E. coli*. DNA sequencing confirmed that all positive clones contained the transposon downstream of the PULL 1012 signal sequence. Plasmid DNA from 15 random ampicillin resistant colonies were prepared using the Qiaspin™ procedure (Qiagen) and DNA sequences were determined from these clones using the two primers specific for the transposon SigA2up (SEQ ID NO: 4) and SeqB (SEQ ID NO: 3). The results are presented in FIG. 1.

In
some instances the secretion signal reporter will be inserted in the host genome within a gene encoding a secreted polypeptide in such a manner that the resulting case for two clones isolated in this experiment: Tn4-12-ab 1(14>777) and Tn4-4-.ab(17>719). The fusion polypeptides of the truncated pullulanase and the secretion reporter β-lactamase retained substantial pullulanase activity in both these two clones, as indicated in FIG. 1 with a box.

The screening step of the present invention may be configured to screen for both the secretion reporter and for an enzyme activity of interest, such as pullulanase, this would allow very fast and efficient screening for specific secreted proteins, not just for secreted proteins as such. In combination with a high-throughput screening assay this technique may be used as a powerful screening tool to isolate genes encoding secreted polypeptides with a screenable activity of particular interest.

Further the gene encoding the secretion reporter comprised in the DNA fragment of the method of the invention may be linked upstream in frame with DNA sequence encoding target sequences for specific proteolytic enzymes, in such a way as after its insertion behind a secretion signal, to provide fusion polypeptides that consist of:
i) the secretion signal and polypeptide encoded by the DNA sequence upstream of the inserted DNA fragment of the invention;
ii) a linker comprising the proteolytic target site; and
iii) the secretion reporter.

Such a configuration would be especially advantageous when screening for secreted fusion polypeptides with an activity of interest, like the two pullulanase fusions above or when screening for antibodies and other biologically active molecules. After isolation of an interesting fusion polypeptide, it could rapidly be produced in a substantial amount by cultivating the primary clone isolated. The obtained fusion polypeptide could be treated with the specific proteolytic enzyme to cleave the target site linking the active polypeptide and the secretion reporter, and substantially pure active polypeptide could be assayed almost immediately. Antibodies directed towards the secretion reporter could be used in an initial purification or isolation step, or the DNA fragment of the invention could comprise a polyhistidine-linker enabling a His/NiTa-coloumb purification. The outlined procedure would circumvent a number of usually difficult and time-consuming steps of cloning and expressing a genomic clone. Examples of fusion linkers are shown in PCT DK00/00296 and mentioned above.

Example 5

Identification of genes coding for a protein containing a signal sequence in a genomic library using the transposon SigA. A subgenomic plasmid DNA library is tagged with the signal trapping mini transposon SigA according to the methods described in Example 2. In this example we use a *Paenibacillus pabuli* genomic library prepared by standard methods. The transformation should be plated out on media 1, 2, and 3 (table 2).

TABLE 2

Typical results of transposition into a *Paenibacillus pabuli* genomic library

| Selection media | Transformants per μg plasmid DNA |
|---|---|
| Medium 1; LB-kan | $10^9$ |
| Medium 2; LB-CAM | $10^6$ |
| Medium 3; LB-CAM, amp | $10^2$ |

Plasmid DNA is isolated from positive clones that grow with chloramphenicol and ampicillin (selection medium 3) and can be sequenced from primers that target sequences located in the transposon. In this way the DNA sequence of the signal trapped gene can be obtained. In many cases, single reads with the two transposon primers will yield most of the genetic sequence of the coding region, alternatively custom primers can be synthesized from the sequence obtained in the first run to complete the gene sequence. Another method is to generate 3–100 times more transformants than needed for full coverage of the library. This permits the transposon to land in the same gene but in a different position of the gene within each clone in several independent transposition events. A computer contig assembly program can be adapted to assemble transposants that represent overlapping regions of the same gene. In this way complete or nearly complete coverage of many secreted genes are obtained.

Example 6

Identification of genes coding for proteins that have a signal sequence, in a genomic library, using the new transposon SigA2

In this example we used a Paenibacillus NN018026 (Deposited on Feb. 08, 2001 at DSMZ as DSM 14046) genomic library that was prepared by standard methods. A subgenomic plasmid DNA library was tagged with the signal trapping mini transposon SigA2 according to the methods described in Example 2. Specifically 1 ul (1.85 ugs) of plasmid DNA library, 4 uls of 5× reaction buffer, 1 ul (200ugs) of SigA fragment and 13 uls of water were used in the standard Finnzymes transposition protocol. The transformation mix was plated out on media 1, 2, and 3 (table 3) and results are shown in table 3.

TABLE 3

Typical results of transposition into a *Paenibacillus* sp. genomic library

| Selection media | Approximate number of transformants per μg plasmid DNA |
|---|---|
| Medium 1; LB-kan | $5.0 \times 10^9$ |
| Medium 2; LB-CAM-kan | $1.4 \times 10^5$ |
| Medium 3; LB-CAM-amp-kan | $1.0 \times 10^3$ |

Plasmid DNA was isolated from positive clones that grew with chloramphenicol (CAM), anamycin (kan) and ampicillin (amp) on selection medium 3, by either Qia-spin™ or Qiaprep turbo™ mini prep (Qiagen Inc.). The plasmid DNA was sequenced with the SigA2up primer (SEQ ID NO: 4) which reads upstream into the signal trapped gene, or SeqB primer (SEQ ID NO: 3) which reads downstream into the trapped gene. In this way the DNA sequence of the signal trapped gene was obtained. In many cases, single reads with only the two transposon primers will yield most of the sequence of the coding region, alternatively custom primers can be synthesized from the sequence obtained in the first run to complete the sequence by 'primer alking' sequencing.

Another method to get the complete sequence is to generate 3–100 times more transformants than needed for full coverage of the library. This permits the transposon to land in the same gene but in different positions of the gene so that several clones can be isolated with each representing independent transposition events. A computer contig assembly program can be adapted to assemble transposants that represent overlapping regions of the same gene. In this way complete or nearly complete coverage of many secreted genes can be obtained, for example the entire sequence of the PULL 1012 pullulanase encoding gene of example 4 could be deduced by contig assembly of a number of the overlapping sequences indicated in FIG. 1.

In this example, signal sequences from several different open reading frames coding for putative proteins were identified. Included are several genes showing sequence similarity to secreted enzymes:

1 pullulanase
3 cellulases
3 chitinases
1 cellubiohydrolase
1 Isomaltodextranase
2 pectate lyases
1 Rhamogalacturonase
1 alginate lyase
1 levanase A total of twelve genes were identified that showed significant sequence similarity to described hypothetical secreted proteins or that contained a sequence that was predicted to be a signal sequences for protein secretion. Two genes were identified which encode putative secreted penicillin-binding proteins. Seven genes were identified as encoding putative secreted solute binding proteins. Two genes encoded putative transmembrane proteins. Genes encoding a putative Integral membrane protein, a substrate binding lipoprotein precursor of an abc transporter similar to bmpA of *Clostridium* sticklandii (50% aa identity) putative membrane protein similar to LPLB PROTEIN (40% aa identity); as well as genes encoding proteins that are located on the outside of the cytoplasmic membrane but are membrane-attached with an anchor peptide such as the putative multiple sugar-binding periplasmic receptor chve precursor of *Agrobacterium tumefaciens* (68% aa identity) or the d-xylose-binding periplasmic protein precursor of *E. coli* (43% aa identity).

Example 7

Using the information from a signal-trapping project. The acquisition of sequence information for all or many of the genes encoding secreted proteins from a gene library is the first step. Most of the trapped genes represent secreted enzymes of known or unknown function. The genes can accordingly be separated into two categories and treated accordingly.

One category of ORFs has significant similarity at the amino acid level to known enzymes. These ORFs can be subcloned into optimal expression vectors, and the constructs can be used to express significant levels of the enzyme, which can then be tested in various applications.

Another category of ORFs does not have significant homology to any known enzymes but are equally interesting. These can be subcloned into expression vectors and expressed in the same way as the known ORFs. Since however, the enzymatic activity (if any) of these ORFs is unknown, no specific assay exists to monitor their activity, and random application testing is appropriate.

Example 8

Eukaryotic Signal trapping with transposons. Many Eukaryotes also secrete enzymes, fungi for example secrete many classes of enzymes including proteases, cellulases and lipases. Because of the relative size and complexity of eukaryotic genomes, genes encoding enzymes are typically expression cloned from cDNA libraries or are identified in EST (expressed sequence tags) sequencing programs. cDNA libraries are made from mRNA isolated from induced biomass from the eukaryote. Methods are known in the art for representing a broad diversity of secreted enzymes in the cDNA library, these methods include: Pooling of biomass material from separate and different induction conditions followed by normalization of the mRNA or cDNA prior to or after cloning.

The basic theory behind signal trapping in prokaryotes and eukaryotes is essentially the same. The main differences are as follows: cDNA libraries depend on the promoter supplied by the vector into which it is cloned. The cDNA library is a subset of the genome that is expressed which means that the hit rate for the transposon into coding regions is higher than signal trapping from prokaryotic genomic libraries.

The signal trapping marker must be specific for the organism one screens in. Typical screening organisms for fungal genes for example are: *Saccharomyces cerevisiae*, *Aspergillus niger*, or *Schizosaccharomyces pombe*. In this example we use an invertase signal trapping system described in: Jacobs, K. A., 1997, Gene 198:289–296.

The modified invertase gene is cloned by PCR to include NotI and EcoRI sites for cloning in frame into the pSigA minitransposon. The bata lactamase is removed by restriction digest and gel purification. A ligation reaction allows the cloning of the invertase gene into the pSigA minitranposon so that the invertase is fused in frame with the left transposon border reading frame exactly as described in the prokaryotic version of pSigA. The completed clone: pSigB is ready for testing in yeast.

The initial test is made on a plasmid containing a cDNA coding for a secreted enzyme that has been expression cloned. The cDNA is the rhgA gene coding for a rhamnogalaturnoase of *Aspergillus aculeatus* (Kofod et al; 1994. J Biol Chem 46:29182–29819). In vitro transposition reactions are performed with 23 ng of SigB minitransposon exactly as described in the bacterial method above. The treated rhgA plasmid is then transformed into yeast cells W3124 in which the native invertase gene is removed. Colonies are plated at high density (1000 colonies per plate) and replica plated on SC media (Sherman, F. 1991. Methods Enzymol., 194:3–21) with sucrose or raffinose; typical results are shown in table 4.

TABLE 4

| Typical results of transposition into pRhgA | |
|---|---|
| Selection media | Transformants per µg plasmid DNA pSigB |
| SC + glucose | 1 × 10$^5$ |
| Replica plated on SC + sucrose | 2 × 10$^3$ |

DNA from the yeast colonies capable of growing on sucrose is rescued into *E. coli* by the method of Strathern and Higgens (1991, Methods Enzymol. 194:319–329). Plasmid DNA is isolated with the Qiaspin protocol (Qiagen) and plasmids are sequenced with YES2.0 vector primers and transposon primers to determine the sequence of the insert. In most cases sequence determination with the primers mentioned is sufficient for complete sequence overage of the cDNA thus allowing analysis of the full length gene and construction of an active expression clone.

Example 9

Using a transposon which carries an origin of replication to identify genes coding for secreted proteins in the genome of a host cell. The advantage of this approach is that the presence of an origin of replication in the transposon allows formation of transposon-plasmids directly from the transposon-tagged genomic host cell DNA. In this example the region from base pair 1763 to 3147 of the plasmid pBR322, carrying the colE1 origin of replication, is PCR-amplified with oligonucleotide primers ori-1 and ori-2:

```
ori-1:  5'-CGCGGATCCTACATCTGTATTAACGAAGCGC      (SEQ ID NO:5).

ori-2:  5'-CGCGGATCCCGTAGAAAAGATCAAAGGAT        (SEQ ID NO:6).
```

The resulting PCR amplicon is cleaved is with the restriction endonuclease BamHI under conditions as recommended by the manufacturer. The SigA2 transposon containing plasmid pSigA2, which contains two BamHI sites, is partially digested with BamHI and the fragment of the PCR amplicon of approx. 1,4 kb is ligated into a single BamHI cleavage site a position 2149. The ligated construct is then restricted with the enzyme BglII to release the desired transposon-replicon fragment from the plasmid backbone. The DNA is then subjected to an additional ligation step and transformed into Escherichia coli DH5α. The transformants are plated on LB chloramphenicol selection. Resulting colonies growing under selection are then replica plated on LB ampicillin and LB chloramphenicol. Several colonies growing only on LB chloramphenicol are selected for plasmid isolation and sequence analysis. A plasmid confirmed to have the correct placement of the ColEI ori in the BamHI position is chosen, this plasmid is designated pMuori.

The transposon fragment of pMuori can be prepared by gel purification in the same way as shown in previous examples. After purification, the isolated transposon can be used in two ways: 1) The transposon can be used in vitro to treat partially digested and size fractionated genomic DNA isolated from the organism of interest. The size fractionated DNA should be in the size range of 1000 base pairs or greater in order increase the likelihood of recovering a full length gene in the subsequent selection. The protocol for such a treatment is the same as in example 4 (Paenibacillus example) however, after the transposition, the resulting mixture is ligated with a DNA ligase to circularize the linear DNA fragments. Resulting circularized DNA is then used to transform the E. coli screening host. Selection regime is exactly the same as in example 4.

A second way to use the Muori transposon is to first create a transposome complex with the transposon and the transposase. One example of such a commercially available system is the Epicentre technologies (USA) "EZ::Tn" system. Essentially, in the absence of magnesium, stable transposome complexes can be formed which cannot insert into foreign DNA until magnesium is present. Upon transformation into the target host, physiological magnesium present in the cell activates the transposome complex thus allowing transposition into the chromosomal DNA in vivo. For our purposes, a signal trapping transposon could also be used for in vivo transposition into the target organism. Chromosomal DNA is then isolated from the treated organism, the DNA reduced to fragments by random shearing or restriction enzyme partial digestion and then ligated with a DNA ligase. The resulting DNA can then be used to transform the appropriate screening host, in this example E. coli DH5α. Selection exactly as in example 4 could also result in recovery of colonies containing a transposon with an origin of replication inserted into a genomic DNA fragment in such a manner as to purvey resistance to the selectable marker; in this case ampicillin. The resulting plasmids are isolated and purified and sequenced with the aid of primers SigA2up (SEQ ID NO: 4) and SeqB (SEQ ID NO: 3).

---

The invention claimed is:

1. A method for identifying a complete coding sequence of a gene of interest from a gene library, wherein the gene encodes a polypeptide carrying a signal sequence for secretion or partial secretion, the method comprising the steps of:
   (a) providing a genomic DNA library or a cDNA library;
   (b) inserting by in vitro transposition into a gene in said library a transposon comprising a polynucleotide encoding a promoterless and secretion signal-less secretion reporter; wherein there is a continuous open reading frame between the transposon and the polynucleotide encoding the secretion reporter;
   (c) introducing the library comprising the inserted transposon into a host cell;
   (d) screening for and selecting a host cell that secretes or partially secretes the secretion reporter;
   (e) identifying the coding sequence of the gene of interest into which the transposon was inserted in the selected host cell, by sequencing DNA flanking the inserted transposon; and
   (f) identifying the complete coding sequence of the gene of interest identified in step (e) by sequencing.

2. The method of claim 1, wherein the complete coding sequence of the gene of interest in step (f) is isolated from the library of step (a).

3. The method of claim 1, wherein the genomic DNA library or the cDNA library is normalized.

4. The method of claim 1, wherein the transposon comprises an origin of replication which is functional in the host cell.

5. The method of claim 1, wherein the secretion reporter is a protein which, when secreted from the host cell, allows said cell to grow in the presence of a substance which otherwise inhibits growth of said cell.

6. The method of claim 5, wherein the secretion reporter is a β-lactamase or an invertase.

7. The method of claim 1, wherein the polynucleotide of the DNA-fragment of step (b) encodes a secretion reporter carrying an N-terminal peptide linker which comprises a specific target site for proteolytic cleavage.

8. The method of claim 1, wherein the sequencing step of step (e) is performed using at least one primer directed to the transposon, or using at least one primer directed to a vector in which the DNA library or cDNA library is cloned.

9. The method of claim 1, further comprising isolating the complete coding sequence of the gene of interest by utilizing the DNA sequence information obtained in the sequencing step of step (e).

10. The method of claim 1, further comprising constructing an expression system which comprises the complete coding sequence of the gene of interest identified in step (f).

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
gaagatctga agcggcgcac ga                                              22

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gcacccaact gatcttcagc a                                               21

<210> SEQ ID NO 3
<211> LENGTH: 21
<212> TYPE: DNA
<213> ORGANISM: Artificial Sequence
<220> FEATURE:
```

```
<223> OTHER INFORMATION: Primer

<400> SEQUENCE: 3
ttattcggtc gaaaaggatc c                                              21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agcgtttgcg gccgcgatcc                                                20

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
cgcggatcct acatctgtat taacgaagcg c                                   31

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
cgcggatccc gtagaaaaga tcaaaggat                                      29
```